United States Patent [19]

Kenkare et al.

[11] 4,154,706

[45] May 15, 1979

[54] NONIONIC SHAMPOO

[75] Inventors: Divaker B. Kenkare, South Plainfield; Clarence R. Robbins, Piscataway, both of N.J.

[73] Assignee: Colgate-Palmolive Company, New York, N.Y.

[21] Appl. No.: 813,569

[22] Filed: Jul. 7, 1977

Related U.S. Application Data

[63] Continuation-in-part of Ser. No. 708,116, Jul. 23, 1976, abandoned.

[51] Int. Cl.$^2$ .................... C11D 1/75; C11D 1/38; C11D 3/26; C11D 7/32
[52] U.S. Cl. .................... 252/547; 252/89 R; 252/544; 252/DIG. 1; 252/DIG. 2; 252/DIG. 13; 252/DIG. 14
[58] Field of Search .................... 252/89, 95, 102, 544, 252/547, DIG. 1, DIG. 2, DIG. 13, DIG. 14; 424/70

[56] References Cited

U.S. PATENT DOCUMENTS

| | | | |
|---|---|---|---|
| 3,001,949 | 9/1961 | Hansen | 252/DIG. 13 |
| 3,156,656 | 11/1964 | Libby | 252/DIG. 13 |
| 3,721,633 | 3/1973 | Ranuato | 252/DIG. 1 |
| 3,808,311 | 4/1974 | Olsen, Jr. et al. | 252/DIG. 13 |

*Primary Examiner*—Mayer Weinblatt
*Attorney, Agent, or Firm*—Richard N. Miller; Murray M. Grill; Herbert S. Sylvester

[57] ABSTRACT

An all nonionic liquid shampoo which includes an amine oxide, a polyoxyethylene hexitan mono-higher fatty acid ester, and at least one of a higher alkoxy polyoxyethylene ethanol, an alkyl glycoside and a mixture of a higher fatty acid lower alkanolamide and polyacrylamide. Optionally, the mixture of higher fatty acid lower alkanolamide and polyacrylamide may be present in the liquid shampoo containing amine oxide, polyoxyethylene hexitan mono-higher fatty acid ester and the higher alkoxy polyoxyethylene ethanol and/or alkyl glycoside. Another optional constituent is a polyethylene glycol higher fatty acid ester. The shampoos are essentially free of ions and are desirably completely free of ionic materials, with the pH being essentially neutral.

12 Claims, No Drawings

NONIONIC SHAMPOO

This application is a continuation-in-part of our U.S. patent application Ser. No. 708,116, filed July 23, 1976, now abandoned.

This invention relates to a nonionic shampoo, useful for washing human hair and leaving it in desirable condition. More particularly, it relates to a liquid shampoo comprising a plurality of nonionic surface active agents and being essentially free of ions, which is capable of washing the hair satisfactorily and leaving it in a manageable state.

Prior art shampoos have usually been based on anionic detergents but have sometimes included nonionic and amphoteric components, too and sometimes have even included cationics. Also, shampoos based largely or primarily on nonionic detergents have been suggested but these have usually included ionic materials, such as salts, acidic or basic materials or materials which may be considered as being anionic or cationic. It is known that anionic materials are capable of breaking salt linkages of keratins and various ionic surface active agents have been shown to be capable of rupturing the keratinic disulfide bond and thereby solubilizing proteinaceous material from the keratin. Disulfide rupture may take place because the ionic materials can alter the isoelectric points of proteins, such as keratin, from normal, at which they are usually most stable and of maximum strength. The isoelectric point of hair varies among individuals but in the absence of added electrolyte the keratin does not significantly react with acids or alkalies near the neutral point, e.g., about 6.5 to 7.5, and thus remains in desired isoelectric condition.

The shampoo of the present invention, preferably being essentially free of ions and comprising only nonionics as surface active agents therein, allows washing of hair without destroying or adversely affecting the salt or disulfide bonds of the keratin and without changing the isoelectric point of the hair, thereby allowing shampooing to be effected without destruction or weakening of the hair. Although various nonionic shampoos may be made in accordance with this invention a preferred product may be based on a mixture of three components, an amine oxide, a polyethoxylated hexitan ester and either a higher alkoxy polyoxyethylene ethanol or an alkyl glycoside or a mixture thereof, in certain proportions in water, preferably deionized water (although other suitable aqueous media may also be employed), and with the shampoo being essentially free of ions. Thus, in accordance with this aspect of the present invention, a nonionic shampoo comprises: (A) about 3 to 25 or 30% of a di-lower alkyl or hydroxy lower alkyl mono-higher alkyl or higher acylamido lower alkyl amine oxide or a mixture thereof wherein the lower alkyls are of 1 to 4 carbon atoms and the higher alkyl is of 10 to 20 carbon atoms; (B) about 2 to 20 or 30% of a polyoxyethylene hexitan mono-higher fatty acid ester having about 10 to 20 carbon atoms in the higher fatty acyl thereof and about 5 or 10 to 100 mols of ethylene oxide per mol; (C) about 6 to 30% of a nonionic detergent selected from the group consisting of higher alkoxy polyoxyethylene ethanols wherein the higher alkoxy is of about 10 to 20 carbon atoms and the ethylene oxide content, including the $CH_2CH_2O-$ of the ethanol, is about 6 to 20 mols per mol, and higher alkyl glycosides, the alkyl of which is of about 10 to 20 carbon atoms, and mixtures thereof; and (D) about 25 to 89% of water. Usually such percentages are 4 to 25, 4 to 15, 10 to 25 and 35 to 82, respectively. In another aspect of the invention it has been found that component C may be replaced by a combination of about 1 to 6% of a higher fatty acid lower alkanolamide wherein the higher fatty acid is of about 10 to 20 carbon atoms and the alkanolamide is a monoalkanolamide or dialkanolamide, the alkanol of which is of 2 to 3 carbon atoms, and about 0.05 to 1% of polyacrylamide. Usually the percentages of such components will be within the ranges of 1.5 to 4 and 0.1 to 0.5, respectively. In a further embodiment of the invention the mentioned percentages of higher fatty acid lower alkanolamide and polyacrylamide may be added to the formula of the first composition, making a 5- or a 6-member composition, exclusive of water content. The percentage of water present, preferably dionized water, will be about 25 to 89% and frequently and preferably is within the 60 to 75% range.

The compositions described above are preferred embodiments of the present invention but in a broader sense the invention may be considered as including nonionic shampoos containing significant proportions of nonionic surface active agents, e.g., a detergent or a plurality of detergents and a foaming agent or a plurality of foaming agents, in an aqueous medium, which are essentially free of ions and are of about a neutral pH. Such a product will preferably have a pH in the range of 6.5 to 7.5, more preferably 6.8 to 7.3, and will preferably contain a polyacrylamide and, optionally, a higher fatty acid alkanolamide.

The amine oxide is essentially nonionic in the pH range of the shampoo. While that pH may be in the 5 to 10 range of commercial products and can still result in a useful shampoo, normally it is within the range of 6.5 to 7.5, preferably 6.8 to 7.3 and most preferably about 7.0. The amine oxide is a surface active material, usually possessing a detersive action in addition to its foaming properties. Of the amine oxides that are useful the di-lower alkyl mono-higher alkyl amine oxides are best and in these the lower alkyls will usually be of 1 to 4 carbon atoms with the higher alkyls being of 10 to 20 carbon atoms, preferably with the lower alkyls being of 1 to 2 carbon atoms and the higher alkyls being of 12 to 16 or 18 carbon atoms. Preferably both of the lower alkyls are the same and more preferably they are methyl and the higher alkyl is myristyl. Examples of other amine oxides that may be employed include diethyl myristyl amine oxide, dimethyl lauryl amine oxide, dimethyl cetyl amine oxide, methyl ethyl myristyl amine oxide and diethyl cetyl amine oxide. Of course, as with the other components of the present composition, the amine oxides will usually be chosen for desired solubility in the aqueous medium employed and for compatibility with the other components of the shampoo.

While the preferred amine oxides are the di-lower alkyl mono-higher alkyl amine oxides, such as are described above, other amine oxides of equivalent surface active properties may also be utilized. Thus, included among these are the products sold under the trade names Ammonyx, e.g., Ammonyx MO, Aromox, Barlox, Chemadox, Conco X, Culverox, Empigen OB, Empigen OY, Hipochem L3A, Romine FLS, Romine FST, Schercamox, Standamox 01, Textamine Oxide LM, Textamine Oxide MP and Varox 743. The identities of such materials are given in McCutcheon's *Detergents and Emulsifiers*, 1969 Annual. Although such materials may have been classified as nonionic, amphoteric and cationic, under the conditions of use and in the present liquid shampoos they are essentially nonionic. Of course, the preferred components of the present shampoos are those amine oxides which are normally liquid and water soluble and which function as foaming agents, foam stabilizers and detergents but for the purpose of this application the amine oxides will be considered to be foaming agents and/or foam stabilizers, both of which are considered under the generic description of foaming agents. Some of the amine oxides described may have the lower alkyls thereof replaced by hydroxy-lower alkyl radicals, e.g., 2-hydroxyethyl, and some may have the higher alkyl mixtures thereof derived from natural materials such as coconut oil and tallow, preferably hydrogenated. In some cases, when a particular higher alkyl is specified in the amine oxide molecule, really a mixture is employed, averaging in chain length the same as the specified alkyl. For example, myristyl may be a blend of alkyls of 12, 14 and 16 carbon atoms. Also, while some unsaturated substituents may be present, normally it is preferred that these be saturated or essentially saturated. In addition to the preferred amine oxides there may also be employed amido amine oxides and polyethoxylated amine oxides, the former of which are marketed under the trade name Textamine Oxide 1839 and Textamine Oxide TA. The latter amine oxides are described in various issued patents, included among which are U.S. Pat. Nos. 3,098,794; 3,206,512; 3,356,727; 3,449,430; 3,697,452; and 3,943,234. These and the Detergents and Emulsifiers publication previously mentioned are hereby incorporated by reference.

Although it is often preferred to use the di-lower alkyl mono-higher alkyl amine oxides (fatty alkyls are much preferred, too), one may also use the amine oxides wherein the lower alkyls or one such group are/is replaced with hydroxy lower alkyl, e.g., hydroxyethyl, hydroxypropyl and/or the higher alkyl is replaced with higher acylamido lower alkyl, e.g. cocoamidopropyl. Thus, the amine oxide may be selected from such group and mixtures of the members thereof.

The polyoxyethylene hexitan mono-higher fatty acid ester has from 10 to 20 carbon atoms in the higher fatty acyl thereof and 4 to 100, preferably 10 to 80 mols of ethylene oxide per mol. Preferably, the hexitan is sorbitan, although mannitan and other hexitans are also often useful, the higher fatty acyl will be of 10 to 16 or 20 carbon atoms, more preferably of 12 to 16 or 18 carbon atoms and most preferably of about 12 carbon atoms, and the number of ethoxies will be from 15 to 80, often preferably about 20. Especially useful is an Atlas Chemical Industries, Inc. product sold under the trade name Tween 20, also known as polysorbate 20. Similarly useful products are sold under similar identifications, such as Tweens 40, 60, 65 and 80, all of which are nonionic surface active agents wherein the higher fatty acyl is lauroyl, palmitoyl, stearoyl or oleyoyl and the number of the mols of ethylene oxide per mol is about 20. Also useful are the polyesters, e.g., the triester Tween 85, but saturated products are preferred. However, of these materials the polyoxyethylene sorbitan monolaurate of the Polysorbate 20 type is usually favored. When the ester includes 80 mols of ethylene oxide per mol it will be preferred that the esterifying fatty acid be of 12 to 14 carbon atoms. Various others of such nonionic surface active agents are listed at page 30 of the *Detergents and Emulsifiers* reference previously mentioned, under Section 32 thereof. In some instances, there may be substituted for the ethoxylated compounds the corresponding non-ethoxylated surface active agents, sold under the Span trademark, and of such materials sorbitan monolaurate (Span 20), a liquid, is preferred. Preferably it will not be employed to replace more than half of the polyethoxylated materials or, stated differently, the content thereof will not exceed that of the polyethoxylated sorbitan monoester in the present shampoos.

The higher alkoxy polyoxyethylene ethanol component of the present liquid shampoos is one wherein the higher alkoxy is of 10 to 20 carbon atoms and the ethylene oxide content thereof, including the $CH_2CH_2O$— of the terminal ethanol, is 6 to 20 mols per mol. Preferably the higher alkoxy is of 10 to 15 carbon atoms and the ethylene oxide content is from 8 to 15 mols per mol. The higher alkoxy may be higher fatty alkoxy or linear alkoxy or may be a more highly branched alkoxy, such as is obtainable from Oxo alcohols made from short chain olefins such as propylene, butylene or isobutylene or mixtures thereof. A preferred compound of this type is that marketed under the trade name Emulphogene BC-720 but other such materials sold under the Emulphogene name and identified as BC-610 and BC-840 may also be employed. Examples of additional materials within the description given are those sold under the trade names Neodol 45-11 (a condensation product of a higher alcohol of about 14.5 carbon atoms and about 11 mols of ethylene oxide per mol of alcohol), Tergitols 15-S-7, 15-S-9 and 15-S-12, Pluradots HA-440 and 540, Plurafacs B-26 and C-17 and Alfonics 1218-60 and 1618-65. However, of the described materials those preferred are of the Oxo alcohol polyethoxylate type, such as Emulphogene BC-720. As examples thereof there may be mentioned tridecyl polyethoxylate of 10 or 15 ethylene oxide groups per mol, tetradecyl polyoxyethylene condensate of 15 mols of ethylene oxide per mol and dodecyl polyoxyethylene condensate of 10, 15 and 20 mols of ethylene oxide per mol. U.S. Pat. Nos. 2,934,568; 2,965,678; and 3,682,849 describe such suitable detergents and are hereby incorporated by reference.

The alkyl glycosides, among which may be mentioned the glucosides, mannosides and galactosides, are preferably higher alkyl glycosides, with the alkyl thereof being of 10 to 20 carbon atoms, preferably of 10 to 14 carbon atoms and more preferably of about 12 carbon atoms. The alkyl is also preferably saturated and linear, although branched alkyls may be satisfactory too. However, they are not readily biodegradable and in this respect are less preferable for this and other components of the present compositions. Of the glycosides the glucosides are preferred and of these that named Surfactant CG-1 by Rohm and Haas is most preferred. Various useful glycosides are described in U.S. Pat. No. 3,721,633 and similar useful materials are mentioned in U.S. Pat. No. 2,974,134, both of which are hereby incorporated by reference. However, it is contemplated that there may be substituted for such materials various other similarly acting sugar ethers, esters and acetals, preferably being the mono-derivatives, although di- and tri-derivatives may also be of use. Similarly, polyoxyethylene derivatives of the sugars or sugar alcohols may also be employed, e.g., with 6 to 20 mols of ethylene oxide per mol, as may be the sugar alcohol analogs of the glycosides.

The higher fatty acid lower alkanolamide wherein the higher fatty acid is of 10 to 20 carbon atoms and the alkanolamide is a monoalkanolamide or dialkanolamide, the alkanol of which is of 2 to 3 carbon atoms, functions in the present nonionic shampoos as a foam stabilizer, viscosity and flow regulator and bodying agent. Preferably the alkanolamide will be a monoalkanolamide and more preferably it will be a monoethanolamide. Also preferably the higher fatty acid will be of 10 to 14 to 10 to 16 carbon atoms and may be derived from natural oils, such as coconut oil or hydrogenated coconut oil. Thus, among examples of suitable alkanolamides there may be mentioned coconut oil fatty acids monoethanolamide or cocomonoethanolamide, coconut oil fatty acids diethanolamide, lauric myristic diethanolamide, lauric monoethanolamide and lauric monoisopropanolamide.

Polyacrylamide has been described in U.S. Pat. No. 3,001,949, wherein it is employed in an anionic shampoo. However the polyacrylamide used in the present invention is of a higher molecular weight, that for the preferred polymer, marketed by Dow Chemical Corp. under the trade name Separan NP-10, being of a molecular weight of about 1,500,000. The preferred molecular weight range is 100,000 to 3,000,000, more preferably 1,000,000 to 2,000,000, but polymers of molecular weights as low as 1,000 and as high as 5,000,000 may also find use although they will usually constitute only minor proportions of mixtures of polyacrylamides. The polyacrylamide or other such polymer or lubricity improving constituent should be water soluble (or at least soluble in the detergent or surface active agent mixture of the shampoo) and should remain soluble therein on storage. In addition to polyacrylamide, other lubricant materials such as silicones and lactates, e.g., myristyl lactate, may be used, some of which materials are sold under the names Ceraphyl 28 and Ceraphyl 50.

With the compositions mentioned above there is preferably employed a preservative, which may be a small proportion of hydrogen peroxide or formaldehyde, usually added as a 30% aqueous solution. It is found that the hydrogen peroxide maintains the amine oxide - hexitan ester - polyoxyethylene ethanol ether or glycoside products free from discoloration during lengthy storage (such formulas may also contain the alkanolamide and polyacrylamide) and it has the advantage of doing this without adding any ionic material to the shampoo. For the amine oxide - hexitan ester - alkanolamide - polyacrylamide formulations formaldehyde is usually the preferred preservative, but it may also be used in the previously mentioned compositions. Freedom from discoloration is also promoted by use of deionized water or water of comparable low ionic content and the use of such water obviates its contributing unwanted ionic compounds to the shampoo. To help to prevent discoloration of dyes and other components that are usually present in shampoos there will usually be present a benzophenone, such as benzophenone-1 or other substituted benzophenone compound, to serve as an ultraviolet light absorber, thereby preventing the ultraviolet light from adversely affecting various other ingredients of the shampoos and undesirably changing the color thereof. Among such ultraviolet light absorbers those preferred are the Uvinuls ®, products of GAF Corporation. Preferred Uvinuls include those numbered 400, 490, D-49, M-40 and D-50, which are normally used in such small quantities that lack of water solubility is not a serious disadvantage. However, Uvinul MS-40, the water soluble derivative of Uvinul M-40, is a preferred water soluble ultraviolet light absorber. These products are effective in the range of 200 to 400 millimicrons and do not darken or decompose upon prolonged exposure to intense ultraviolet light rays. Rather than utilizing the substituted benzophenones, all of which are referred to in the present claim as benzophenones, because it is that part of the molecule which is most significant as an ultraviolet light absorber, one may employ other ultraviolet absorbers, such as the substituted acrylonitriles, of which Uvinuls N-35 and N-539 are examples. The employment of color stabilizers, such as hydrogen peroxide, formaldehyde and benzophenone derivatives, is more important in the case of clear shampoos, a most preferred class of embodiments of this invention; however, one may also utilize them in opaque, translucent or emulsion shampoos.

The particular combination of amine oxide and hexitan monoester, with polyoxyethylene ethanol ether and/or alkyl glycoside optionally present, furnishes a balanced, completely nonionic surface active agent system which has desirable foaming, lathering and detersive properties despite the fact that nonionic surface active agents are usually deficient in such properties. The alkanolamide, in the particular combination recited, improves the foam and lather characteristics, while also exerting desirable modifying effects on the product flow characteristics and hair treatment and the polyacrylamide acts similarly, improving the lubricity of the foam and the feel of the hair treated and exerting some thickening effect on the shampoo. However, despite the presences of the alkanolamide and the polyacrylamide in the shampoos, it is very often desirable to further improve the viscosity and pour properties of the liquid shampoos and to accomplish this it has been found to be useful to include in those compositions a polyethylene glycol higher fatty acid ester of an average molecular weight in the range of 2,000 to 8,000, preferably 4,000 to 7,000, and most preferably, about 6,000, wherein the fatty acid moieties thereof are each of 12 to 20 carbon atoms, preferably of 16 to 20 carbon atoms and most preferably of about 18 carbon atoms. It is preferred that the polyethylene glycol ester be a diester and most preferred of these compounds is the polyethylene glycol distearate of an average molecular weight of about 6,000.

As was previously mentioned, the water employed is preferably deionized and most preferably is completely ion-free. However, sometimes ordinary tap water may be utilized, providing that it is comparatively low in ionic content so that the product resulting is essentially free of ionic materials and has a conductivity below 5,000 micromhos/cm. Preferably the conductivity will be below 1,000 micromhos/cm. which corresponds to about 0.5 g./l. of NaCl. Most preferably, conductivity readings will be 200 micromhos/cm. or lower.

In addition to maintaining the ionic content of the water low the various other components of the shampoo are also held low in ionic constituents so as to maintain the ionic content of the final product low, like that of the deionized water mentioned. As a result, the present shampoo leaves the hair clean, yet manageable and of desirable feel, combability, gloss, strength, appearance, sheen and manageability.

In addition to the previously mentioned constituents of the liquid shampoo one may also employ normal and conventional adjuvants, providing that they are nonionic. Thus, there may be used various coloring agents and perfumes; thickeners, such as hydroxypropylmethyl cellulose, methyl cellulose, polyvinyl alcohol and polyvinyl pyrrolidone; pearlescing agents and opacifiers; solvents, such as ethanol, preferably in the form of a specially denatured alcohol such as SD-40, and glycols (ethylene glycol is useful as a clarifying agent, to prevent high and low temperature cloudings of desirably clear shampoos); lubricants, such as mineral oil and higher fatty alcohols, e.g., cetyl alcohol, stearyl alcohol; antibacterial materials; preservatives; etc. The proportion of such adjuvant materials, in total, will normally not exceed 10% of the shampoo, preferably being no more than 5% thereof and often being less than 2% thereof. The percentages of most of such individual components will be less than 2%, often being less than 1%.

The proportions of the various components of the nonionic liquid shampoo are maintained within the certain ranges given for best effects. Thus, in the amine oxide - hexitan monoester - polyoxyethylene ethanol ether or alkyl glycoside compositions, there are about 3 to 30%, preferably 4 to 25%, more preferably 5 to 10% and most preferably about 7.5% of the mentioned type of substituted amine oxide; about 2 to 30%, preferably 4 to 15%, more preferably 5 to 10% and most preferably about 7.5% of polyoxyethylene hexitan mono-higher fatty acid ester; about 6 to 30%, preferably 10 to 25%, more preferably 15 to 20% and most preferably about 17% of the higher alkoxy polyoxyethylene ethanol or alkyl glycoside or mixture thereof; and about 25 to 89% preferably 35 to 82%, more preferably 60 to 75% and most preferably about 64% of water. The higher fatty acid lower alkanolamide, when present (which is highly desirable), is within the range of about 1 to 6%, preferably 1.5 to 4% and most preferably is about 2.5%. Similarly, the polyacrylamide, when employed (also highly preferred), is about 0.05 to 1% of the product, preferably 0.1 to 0.5% and most preferably about 0.2%. The hydrogen peroxide or other stabilizer content is normally within the range of about 0.01 to 0.5%, preferably being 0.05 to 0.5%, more preferably 0.1 to 0.3% and most preferably about 0.2% for hydrogen peroxide but it may be lower e.g., 0.01 to 0.3%, for other preservatives, such as formaldehyde. Such figures are on active ingredient bases as charged. Products employed preferably omit all ionic materials.

For the amine oxide - hexitan monester - alkanolamide - polyacrylamide shampoos the ranges of proportions of constituents are about 3 to 30%, preferably 4 to 15%, more preferably 5 to 10% and most preferably about 8% of the di-lower alkyl or hydroxyalkyl mono-higher alkyl or acylamido lower alkyl amine oxide, about 2 to 30%, preferably 10 to 30%, more preferably 15 to 25% and most preferably about 19% of the polyoxyethylene hexitan mono-higher fatty acid ester, about 1 to 6%, preferably 1.5 to 4%, more preferably 2 to 3% and most preferably about 2.5% of higher fatty acid lower alkanolamide, about 0.05 to 1%, preferably 0.1 to 0.5%, more preferably 0.1 to 0.3% and most preferably about 0.2% of polyacrylamide and about 25 to 89%, preferably 35 to 82%, more preferably 60 to 75% and most preferably about 67% of water. The contents of polyethylene glycol higher fatty acid ester, ethylene glycol (anti-clouding agent), when present formaldehyde and benzophenone compound, in preferred compositions of this type are respectively about 0.2 to 8%, preferably 0.5 to 5%, more preferably 1 to 3% and most preferably about 2%; about 0.5 to 5%, preferably 1 to 5%, more preferably 1 to 3% and most preferably about 2%, about 0.01 to 0.2%, preferably 0.01 to 0.1%, more preferably 0.01 to 0.05% and most preferably about 0.03% of formaldehyde; and about 0.01 to 0.2%, preferably 0.01 to 0.1%, more preferably 0.01 to 0.05% and most preferably about 0.03% of benzophenone compound.

The proportions of the various surface active components to one another, within the percentage ranges previously given, will normally be controlled to maintain a desired balance of properties in the product. Thus, in the first type of shampoo (with the polyoxyethylene oxide ethanol and/or glycoside) the proportion of amine oxide:polyoxyethylene hexitan mono-higher fatty acid ester:higher alkoxy polyoxyethylene ethanol and/or alkyl glycoside will usually be 1:0.5 to 2:1 to 4, with the total proportion of the nonionic detergents, e.g., last three mentioned surface active agents, to amine oxide being in the range of 1:1 to 7:1. For the second type of shampoo, omitting the polyoxyethylene ethanol ether and/or glycoside and including alkanolamide and polyacrylamide, the proportion ranges of the amine oxide to hexitan monoester will usually be 1:1 to 5, with such proportions to alkanolamide and polyacrylamide usually being 1:0.0 to 0.5 and 1:0.1 to 0.05.

In a broader aspect of the present invention other nonionic surface active agents may be employed in the aqueous medium, including at least one which, like the amine oxide (it may be the amine oxide), is a foaming agent or is primarily a foaming agent and at least one of which is a detergent or primarily a detergent. The total of nonionic surface active agents including any alkanolamide present, is usually within the range of 11 to 90%, preferably 15 to 50% and more preferably 20 to 40%, with the balance, except for the alkanolamide and polyacrylamide and the mentioned adjuvants, being water. Of course, the percentages will usually be adjusted to provide sufficient water or water-solvent system to satisfactorily dissolve all the shampoo components, and in this respect it should be kept in mind that liquid nonionic components will normally be employed when water contents are low. In this described broader aspect of the invention, although it will be preferred to employ the same surface active agents as were previously described or equivalents thereof, such as were previously mentioned, a wide variety of detergents may be substituted, at least in part, for the mentioned detergent components. Thus, preferably at least 50% of the detergent components of the shampoos will be polyoxyethylene hexitan mono-higher fatty acid ester (with higher alkoxy polyoxyethylene ethanol and/or alkyl glycoside) and at least 50% of the foaming agent component will be amine oxide. Other useful nonionic detergents and nonionic foaming agents (nonionic at the pH of the shampoo) include higher and middle alkyl phenol polyoxyethylene ethanol of 5 to 30 mols of ethylene oxide per mol; ester analogs of the ethers previously described; block copolymers of ethylene oxide and propylene oxide such as those sold under the trademark Pluronic; and various others of the well-known nonionic detergents, such as those sold under the trademarks Plurafac C-17; Igepal CO-710; Conco XAM; Triton X-100; Glucamate Sesq. 15X (also 10X, 100X, 40X, 100X and 120X); and Igepal RC-630. Other nonionics are described in the reference *Detergents and Emulsifiers,* previously mentioned, especially in classes 5, 7, 8, 10, 11, 32 and 34, appearing at pages 23–32. Such materials are described in more detail elsewhere in the reference, as indicated.

In such broad aspect of the invention it is also desirable to employ the nonionic polyacrylamide but other thickening and foam modifying agents may also be utilized, such as Carbowax, Polyox, polyvinyl alcohol or methyl cellulose, so long as such are soluble and stable and contain no ionics. Foam stabilizing equivalents of the alkanolamides are also useful in this broader aspect of the invention and it is desirable to utilize the same proportions, previously described for the various components, so that the content of the plurality of nonionic surface active agents is about the same. When, in accordance with a broader aspect of the invention, the foaming agent is an amine oxide, it contains at least 12 carbon atoms (aromatic amine oxides are contemplated as sometimes useful) and the amount of the (plurality of) nonionic detergent(s) present is from 1 to 7 times the amount of such amine oxide. In such case the pH is from 6.5 to 7.5 and the water content is in the range of 25 to 89%, with the more preferred ranges being as previously given. Preferred compositions under this broader aspect of the invention include as one of the nonionic detergents the polyoxyethylene hexitan mono-higher fatty acid ester. Such compositions will also preferably include the polyacrylamide and, optionally, alkanolamide of the type mentioned and in the proportions previously given.

The present shampoos are readily made by simple mixing methods from readily available components which, on storage, do not adversely affect the entire composition. Thus, the products are capable of being made in desired clear form or in cloudy, opaque or opalescent form. The viscosities are adjustable by changing the total percentage of active ingredients and by modifying the percentages of polyacrylamide and other adjuvants. Also, solvents and thickeners may be utilized. In all such cases the product made will be pourable from a relatively narrow mouth bottle (1.5 cm. diameter) and the shampoo will not be so thin as to run off the hair or hands like water during use. The viscosity of the shampoo will normally be about that of glycerin at room temperature, e.g., about 1,000 centipoises, but the viscosity may be in the broader ranges of 250 to 2,000 and 50 to 5,000. Its viscosity may approximate those of commercially acceptable shampooes now on the market. Instead of measuring viscosity directly, as by a viscosimeter, one may employ standard laboratory flow tests, in which flow times through a restriction or tube length under a reproducible head are measured. The shampoo viscosity and the shampoo itself remain stable on storage for lengthy periods of time, without color changes or settlings out of any insoluble materials.

The product, especially in its preferred forms, has unexpectedly desirable properties. For example, the foam quality and lubricity is comparable to standard shampoos based on triethanolamine lauryl sulfate. Further, such shampoos clean the hair exceptionally well and leave it easy to comb, manageable and of low raspiness. Upon running comparative experiments the preferred products are found to be superior to a leading commerical anionic-based shampoo by both laboratory and practical use tests, with respect to being less drying, leaving the hair with a softer feel, being less raspy during wet combing, producing fewer split ends after shampooing, and being easier to comb and causing less flyaway effect. Such preferred experimental products are also preferred for foam appearance and for foam stability, compared to the control commercial product. Another preferred experimental shampoo of the invention is significantly better than the same commercial product in being less drying, leaving the hair with a softer feel and leaving it easier to comb, having less fly-away effects and in appearance and feel of the foam. Additionally, the present shampoos are non-irritating the the conjunctiva although they desirably cause a smarting to warn of their presence. Foam volume and build-up rate are not superior to those of most of the commercial products based upon anionic detergents, but the experimental formulations are generally preferred on an overall basis compared with such commercial shampoos. The desirable differences in properties leading to such general preference are attributed at least in part to the nonionic and non-ionic nature of the product and the balanced contents of the nonionic detergent(s), foaming agent and other functional components described.

In particular, as has been stressed, it is important that the ionic content of the shampoo be minimized and this is usually accomplished by using components that are low in ionic contents or in which such content is nil. It has been found that commercial shampoos of the anionic types have conductivities in the range of 20,000, to 52,000 micromhos/cm. but the present products of the invention have conductivities below 5,000, usually below 2,000 and preferably below 1,000 micromhos/cm. Thus, using a formula including Emulphogene BC-720 a reading of 750 micromhos/cm. results while with a product based on Surfactant CG-1 the reading is 1450 micromhos/cm. The conductivity of a preferred amine oxide - hexitan ester - alkanolamidepolyacrylamide shampoo of the invention is 721 micromhos/cm. Comparatively, the conductivity of deionized water is 3 and that of tap water ranges from 200 to 1,000 micromhos/cm. These conductivity readings correspond to about 0.5 g./l. of NaCl per 1,000 micromhos/cm. All readings are taken on a Hach Conductivity Meter, Model No. 2511, using the micromhos/cm. scale.

Although the non-ionic nature of the invented products is considered of great importance in producing the desired hair washing and conditioning, etc. results, it and the particular mixtures of components recited may also contribute significantly in making the present shampoos of desired thickness and foaming power. That the shampoos should be good foamers and of increased viscosity is unexpected in view of the facts that nonionic detergents usually are poor foamers and of low viscosity. Also, in aqueous systems mixtures of nonionic surface active agents often tend to gel but the present compositions do not. They remain gel-free at desired initial viscosity during usual lengthy storage periods before use.

The unexpectedly good foaming power of the nonionic shampoo is measurable by a standard test used in the laboratories of the assignee of the present invention. In this test artificial sebum is used to simulate the effects of washing human hair. The sebum is a complex mixture of 45% of mixed saturated and unsaturated fatty acids, 10% paraffin, 15% spermacetti, 20% olive oil, 5% of cholesterol and 5% of squalene. 15 Grams of the shampoo to be tested are diluted with deionized water to 100 grams and are added to a 150 ml. beaker after 3 grams of the artificial sebum has been smeared over the beaker wall. The diluted shampoo is then heated to 42° C. with stirring and is transferred quickly to a 500 ml. graduated cylinder at the same temperature. The cylinder is then shaken 20 times, preferably mechanically, using a special machine, but manual shaking may be employed too.

At the completion of the shaking the cylinder is uncapped, set vertical and a stop-watch is started. The level of the foam where it is most uniform is read and when the water line reaches the 100 ml. mark on the graduate the watch is stopped. The mentioned foam height is a measure of the foaming power of the shampoo under actual use conditions and the time is indicative of the foam stability. By this test an Emulphogene BC-720 formula, at 15% dilution reads 250 ml. and 22 seconds and a CG-1 formula at the same dilution reads 275 ml. and 24 seconds. Similar foaming effects result from the amine oxide - hexitan monoester - alkanolamide - polyacrylamide shampoos of this invention. In contrast, shampoo based on only a nonionic detergent of the type employed, in the same total detergent quantity, reads about 50 ml. and 7 seconds. To be a good product it is considered that the reading for foaming power should be at least 150 ml. and preferably it is at least 200 ml. with maximum at about 450 ml.

The following examples illustrate but do not limit the invention. Unless otherwise mentioned, all parts in the examples and elsewhere in the specification are by weight and all temperatures are in ° C.

EXAMPLE 1

| | Parts |
|---|---|
| Emulphogene BC-720 (Tridecyloxy polyethoxy ethanol of ten ethoxy groups, mfd. by GAF Corp., 100% active ingredient) | 17.3 |
| Tween 20 (Polyoxyethylene (20) sorbitan monolaurate, mfd. by ICI Industries, 100% active ingredient) | 7.5 |
| Ammonyx MO (Myristyl dimethylamine oxide, mfd. by Onyx Chemical Co., 30% active ingredient in water) | 25.0 |
| Cocomonoethanolamide (85% active ingredient) | 2.5 |
| Separan NP-10 (water soluble polyacrylamide of molecular weight of about 1,500,000, mfd. by Dow Chemical Co., 100% active ingredient) | 0.2 |
| Hydrogen peroxide (30% aqueous solution) | 0.5 |
| Perfume | 1.0 |
| Deionized water (3 micromhos/cm. conductivity) | 46.0 |

A shampoo of the above composition is made in the following manner. First, the Emulphogene BC-720 is added to a clean mixing tank, with the agitator on, and the Ammonyx MO, Tween 20 and cocomonoethanolamide are added sequentially, with continued agitation. The mix is then heated to 68° C., until the cocomonoethanolamide is melted and/or dissolved. The hydrogen peroxide solution is then admixed with the mentioned nonionics and mixing is continued for about ½ hour, in which time the perioxide destroys any free amines or other harmful impurities that may be present. The mix is then cooled to 38° C.

In a separate mixer the Separan NP-10 is gradually added to the formula weight of deionized water, with the mixer on. Addition is effected carefully and slowly (the polyacrylamide is sprinkled in) to avoid the production of "fish eyes" in the mix. After dissolving of the polyacrylamide the solution thereof is added to the first mixing tank with agitation and is blended with the nonionics, such mixings being at room temperature. Subsequently the perfume is admixed with the balance of the composition and mixing is continued for another ½ hour.

The product made is an excellent shampoo of desired viscosity, foaming power, foam stability, low conductivity and good shampooing effects. The viscosity is about 1,000 centipoises at 21° C. and the conductivity, using the Hach Conductivity Meter, is 750 micromhos/cm. The foaming power is 250 ml. and the foam stability is 22 seconds, by the test method previously described. In comparison, a commercial shampoo based on triethanolamine lauryl sulfate detergent has a conductivity of about 22,000 micromhos/cm., a viscosity of about 1,500 centipoises, a foaming power of about 380 ml. and a foam stability of 60 seconds.

In panel evaluations of the experimental shampoo, compared to a different commercial product, in actual shampooing, the experimental formula was adjudged significantly better in being less drying, producing a softer feel for the wet hair, leaving the wet hair easier to comb, being less prone to accumulate static charges (less fly-away) and having a foam of better appearance and feel. Additionally, the experimental product was judged better in almost all hair effect properties, with the control only being about equal to it in curl retention. In foaming properties other than those mentioned the experimental was better in rinsability, the control was better in foam build-up rate and the foams were about equal in volume and stability.

In the shampooing described herein and in subsequent examples the human hair is washed on the head by wetting the hair with warm tap water at about 42° C., applying 15 grams of shampoo to the hair, lathering it into the hair for a minute, rinsing with warm tap water for 30 seconds, re-lathering with 7 grams of shampoo for a minute and rinsing off for 30 seconds, after which the hair is towel dried and dried further with an automatic hair dryer.

EXAMPLE 2

| | Parts |
|---|---|
| Surfactant CG-1 (higher alkyl [10 to 18 carbon atoms] monoglucoside, mfd. by Rohm and Haas, 70% active ingredient in aqueous medium) | 24.7 |
| Tween 20 (Polyoxyethylene (20) sorbitan monolaurate, mfd. by ICI Industries, 100% active ingredient) | 7.5 |
| Ammonyx MO (myristyl dimethylamine oxide, mfd. by Onyx Chemical Co., 30% active ingredient in water) | 25.0 |
| Cocomonoethanolamide | 2.5 |
| Separan NP-10 | 0.2 |
| Perfume | 0.8 |
| Deionized Water (3 micromhos/cm. conductivity) | 38.8 |
| Hydrogen peroxide (30% aqueous solution) | 0.5 |

The above product is made according to the method previously described in Example 1, with the CG-1 material being substituted for the Emulphogene. The product made, like that of Example 1, is an excellent shampoo, superior in many characteristics to conventional, commercial anionic-based products. The viscosity is also about 1,000 centipoises and the Hach Meter conductivity is 1,450 micromhos/cm. The foaming power is 275 ml. and the foam stability is 24 seconds. These figures establish the product, like that of Example 1, to be of a desirable viscosity, which allows the product to be held on the hands and hair without objectionable dripping thereof, and to be of foaming properties that are comparable to those of the anionic-based detergent shampoos.

When tested in half-head tests against other shampoo compositions of the anionic type, which are commercial products, the experimental product is shown to be especially good in a wide variety of properties. For example, against a leading product the experimental was better in being less drying, leaving the hair feeling softer, leaving the tresses less raspy during wet combing, producing significantly fewer split ends on repeated shampooings, and leaving the hair easier to comb. Against a second leading shampoo the experimental was preferred for soft feel of the hair, both wet and dry, being less drying, better for snags removal, comb-slip and lack of raspiness. The invented product is superior to a third commercial shampoo in soft-feel, less dryness, easier snag removal, better comb-slip and less raspiness. Similar results were obtained with respect to the other four commercial shampooes tested against the experimental formula. Although the commercial anionic-based products were superior in some foaming properties, the experimental also was sometimes superior in such characteristics and even when foaming was not as good for the invented product, the foam was comparable, not decidedly inferior, as one might have expected from a shampoo in which the active ingredients are nonionic.

EXAMPLE 3

The products of Examples 1 and 2 are made but omitting the polyacrylamide, replacing it with water. The shampoos resulting are of satisfactory properties but the appearance and feel of the foam are not as good as when the polyacrylamide is present. In another variation of the formula the cocomonoethanolamide is omitted from the four formulas mentioned and a noticeable diminution in foam properties is noted, although the desirable effects on the washed hair are essentially the same. In other words, a product based on only the foaming agent and the two detergents, without any ions present or with essentially no such ions present (meeting applicants' standards of conductivity as previously set forth) is a good shampoo but can have various important properties thereof further improved by the addition of polyacrylamide and CMEA or their equivalents. When the peroxide treatment step is omitted (and formaldehyde or other preservative is not employed) some product discoloration is noted but the shampoo still is of good hair conditioning properties and this is the situation even when the polyacrylamide and CMEA are also omitted.

EXAMPLE 4

|  | Parts |
| --- | --- |
| Surfactant CG-1 | 32.9 |
| Tween 20 | 10.0 |
| Ammonyx MO | 33.3 |
| Higher fatty alcohol ($C_{12-14}$) | 1.0 |
| Ethanol (SD-40) | 7.0 |
| Perfume | 0.5 |
| Deionized water | 15.3 |

The shampoo is made in the same general manner previously described and is found to be of useful viscosity, foaming properties and conductivity and also leaves the hair feeling exceptionally clean, easy to comb after shampooing and of low electrostatic charge. Such shampoo, free of harsh acids, alkalies, salts and other sources of ions, is a good detergent for the hair and leaves it in good shape and manageable.

EXAMPLE 5

The formula of Example 1 is varied by having the Emulphogene replaced by Triton X-100; Plurafac C-17; Glucamate Sesq. 60X; Glucamate Sesq. 120X; Glucamate Sesq. 15X; Glucamate STE 40X; Glucamate STE 100X; Glucamate STE 10X; Glucamate CO 10X; Glucamate CO 100X; Glucamate CO 40X; Glucamate LAV 10X; Glucamate LAV 40X; Glucamate LAV 100X; and IL 727 and the products resulting all have foaming powers in the 150 to 300 ml. range. However, some have lower foam stabilities, such as those with Glucamate Sesq. 15X & Glucamate STE 10X. The others are of good foaming stabilities and powers, whether or not they contain the Separan. All are good shampoos and leave the hair manageable.

EXAMPLE 6

The experiments of Examples 1 and 2 are repeated but with the proportions of the various nonionic constitutents, the polyacrylamide and the CMEA being varied ±10%, 20% and 30% while still being maintained within the described ranges. When the ionic content is maintained low, with the conductivity being less than 5,000 micromhos/cm. and the pH being in the 6.8 to 7.3 range, the products made are good shampoos and leave the hair washed with them in desired condition, usually being superior to anionic detergent-based shampoos on the market. When the conductivity is held to no more than 2,000 micromhos/cm. the pH may be increased to 8.0 for these and other described products of this invention without losing the desirable hair washing and conditioning effects mentioned. However, it is strongly preferred to maintain the pH as close to neutral as is feasible and usually it will be within the 6.5 to 7.5 range, preferably 6.8 to 7.3, although the 6.0 to 8.0 range is also feasible for this and other formulations of the invention.

EXAMPLE 7

The experiments of Examples 1 and 2 are repeated but with the Emulphogene and CG-1 replaced sequentially by Neodol 45-11; Neodol 25-7; Plurafac C-17; Plurafac B-26; Triton X-100; Igepal RC-630 and Pluradot HA-440; the Tween 20 being replaced sequentially with the others of the Tweens mentioned earlier in this specification and with the others of the nonionic detergents mentioned (at least two different detergents being used); and with the Ammonynx being replaced with other Ammonyxes and amine oxides and other foaming agents, e.g., diethyl cetyl amine oxide, dimethyl lauryl amine oxide, ethyoxylated decyl dimethyl amine oxide, hydroxylauryl dimethyl amine oxide and any other foaming agents which are nonionic in nature. Also, the Emulphogene and CG-1 components are used in mixture with each other, usually at about equal weights and other mixtures are also employed. In addition, the CMEA may be replaced by an "equivalent" such as LMDEA (lauric myristic diethanolamide). The products resulting are all low ionic shampoos of good hair treating properties, although usually not as good as the preferred products of the invention.

EXAMPLE 8

|  | Parts |
| --- | --- |
| Polysorbate-20 (100% active ingredient) | 19.0 |
| Myristyl dimethyl amine oxide (30% active ingredient) | 25.0 |
| Coconut oil fatty acids (100% AI) monoethanolamide | 2.5 |
| Polyacrylamide (Separan NP-10 premium, 100% AI) | 0.2 |
| Polyethylene glycol 6,000 distearate (100% AI) | 2.0 |
| Formalin (30% aqueous formaldehyde solution) | 0.1 |
| Benzophenone | 0.03 |
| D&C Red No. 33 (0.01% aqueous solution) | 0.1 |
| D&C Orange No. 4 (1% aqueous solution) | 0.1 |
| Perfume | 1.0 |
| Deionized water | 49.97 |

The shampoo is made in essentially the same manner as that described in Example 1, with the amine oxide being stirred in a clean mixing tank while the Polysorbate-20 and coconut oil fatty acids monoethanolamide are added sequentially, with agitation continuing. The mix is then heated to melt and dissolve the coconut oil fatty acids monoethanolamide (or the CMEA can be melted initially). The polyacrylamide is gradually added to the deionized water in a separate mixer, with the mixer on, as described in Example 1, and after it is dissolved the solution thereof is added to the mixture of amine oxide and sorbitan ester in the first mixing tank, with agitation, and is blended with the nonionic constituents therein at room temperature. Subsequently, the formalin, benzophenone, dyes and perfume are sequentially mixed in to produce the final shampoo.

The product made is an excellent mild shampoo, less damaging to the hair and less irritating to the scalp, skin and mucous membranes than control anionic-based shampoos, having desirable viscosity (30 to 45 seconds on a standard flow meter), foaming power, foam stability, low conductivity and good shampooing effects on human hair. The viscosity is similar to that of the product of Example 1, as are the foaming power and foam stability and conductivity. The shampoo is stable on storage, is found to be of desirable foaming and lathering properties in practical use tests (actual shampooing) and leaves the hair soft and more manageable than when an anionic shampoo is employed and less prone to accumulate static charges.

It will be noted that in the described formula the Emulphogene BC-720 and Surfactant CG-1 have been omitted, the proportion of Polysorbate-20 has been increased and cocomonoethanolamide and polyacrylamide are present. For best results in the manufacture of the product of this example and similar products from which the polyethoxyethanol ether and glycoside components have been omitted, the combination of alkanolamide and polyacrylamide should be present but the proportions thereof may be varied within the ranges described previously. When either the amide or the polyacrylamide is omitted the product resulting is less satisfactory as an all-nonionic shampoo but may be acceptable, even for commmercial use, when product standards are somewhat lower. Instead of cocomonoethanolamide, lauric myristic monoethanolamide may be used, with similar results and lauric monoethanolamide and myristic monoethanolamide may be substituted, as may be lauric myristic diethanolamide but the monoethanolamides are best, as are the coconut oil fatty acid amides. Similarly, other polyacrylamides are useful and are employed, having molecular weights of 1,000,000 and 2,000,000.

EXAMPLE 9

A variation (1) of the formula of Example 8 is made, utilizing 25 parts of Ammonyx MO (30% AI), 20% of Tween 20, 2.5% of cocomonoethanolamide, 0.2% of Separan NP-10 (premium), 1% of perfume and 51.3% of deionized water. The product resulting is a clear shampoo of excellent appearance and stability, having a viscosity of about 10 seconds on a laboratory flow meter, conductivity of 721 micromhos/cm. and a cloud point of 2° C. and a clear point of 6° C., producing a very satisfactory and stable foam and leaving the hair easier to comb (wet combing) than a commercially very successful anionic detergent based shampoo and as good as such shampoo in dry combing properties. When either the Separan or cocomonoethanolamide component is omitted the product made is less satisfactory as a shampoo, with significant changes in foaming observed when cocomonoethanolamide is omitted and poorer product lubricity and poorer combing properties resulting when the polyacrylamide is not present.

In minor variations of this formula (2) the percentage of cocomonoethanolamide is increased to 3.0% while that of Tween 20 is decreased accordingly to 19.5%; (3) the CMEA content is increased to 3.5% and the Tween 20 content is dropped to 19.0%; or (4) the Separan NP-10 content is increased to 0.25% while that of the deionized water is decreased slightly accordingly. The products resulting are all good shampoos of properties like formula (1) of this example, but the viscosity changes, being 15 seconds for (2), 17 seconds for (3) and 11.3 seconds for (4).

In an additional variation of the invention of this example 0.5% of a 30% aqueous solution of hydrogen peroxide replaces an equivalent percentage of the deionized water and the batch is cooked for about 45 minutes at a temperature of 66°–71° C. after the addition of the peroxide so that it might react with any destabilizing free amines present. The product resulting is a stable shampoo of a viscosity of about 11.5 seconds, with other properties being those those of the comparable products previously described. Good products within the invention are made when the cocomonoethanolamide content of (1) is increased to 3.5% and 4.5%, respectively, with the Ammonyx MO contents being decreased to 21.7% and 18.3%, respectively, while deionized water contents are increased to 53.6% and 56.0%, respectively. The products resulting yield excellent creamy lathers and are as good as or better than the leading commercially successful shampoo in foaming characteristics. In other variations of the described base formula of this example the proportion of Tween 20 or other polyoxyethylene sorbitan monolaurate utilized is decreased to 19%, the percentage of CMEA is increased to 3.5%, the percentage of perfume is decreased to 0.75%, 0.05% of formalin is present and the deionized water content is increased to 51.5%. In still other variations, the Ammonyx MO is replaced by Ammonyx CDO and Aromox C/12W, respectively. In all such cases the product resulting is an excellent shampoo, particularly noted for very good foaming effects.

The formulas of this example are further improved with respect to light stability by the addition thereto of 0.02 to 0.04%, e.g., 0.03%, of a benzophenone compound, preferably Uvinul ®, e.g., Unvinul 400, or other such ultraviolet absorbing chemical. Similarly, the products of this example and Example 8 are improved with respect to high temperature clouding and storage stability by addition thereto of 1 to 3%, e.g., 2%, of ethylene gylcol.

EXAMPLE 10

The experiments of Examples 8 and 9 are repeated but the proportions of the nonionic surface active agents, polyacrylamide, alkanolamide, polyethylene glycol ester and other components are varied ±10%, ±20% and ±30%, while still being maintained within the described ranges. The ionic content is maintained low and conductivities of the products are less than 5,000 micromhos/cm., with the pH's, as in Examples 8 and 9, being in the 6.8 to 7.3 range. The products made are good, mild shampoos and leave the hair washed with them in desired condition, usually being superior to anionic detergent-based shampoos on the market. The products are of desirable storage stability, viscosity, pour characteristics, lathering properties and detergency, are mild to the hair and scalp and leave the hair easy to comb and manage. Similar effects are also obtained when, in place of the particular components described, others within the invention and recited in the specification are substituted. Also, the viscosities are increased to about 1,000 cp., so that the flow rates are about 30 to 45 seconds, using a standard flow meter, when about 2% of PEG 6,000 distearate or similar polyethylene glycol mono- or diester is present in the formulations of Examples 9 and 10. Although various Tween type nonionic detergents may be substituted, with the product resulting being of essentially the same properties, in this and the other examples, it is preferred to use those of 10 to 80 ethylene oxides per mol, preferably 10 to 30. Other ranges of ethylene oxide current are 10 to 100, preferably 20 to 80 mols per mol.

EXAMPLE 11

|  | Parts |
| --- | --- |
| Polyoxyethylene (80 mols ethylene oxide) sorbitan monolaurate | 19.0 |
| Dimethyl myristyl amine oxide (30% active ingredient) | 25.0 |
| Cocomonoethanolamide (85% active ingredient) | 2.5 |
| Polyacrylamide | 0.2 |
| Polyethylene glycol 6,000 distearate | 2.0 |
| Formalin | 0.1 |
| Perfume | 1.0 |
| Deionized water | 50.2 |

When the above components are combined in the manner previously described a very thick liquid shampoo is obtained which is of good foaming characteristics and is mild to the conjunctiva and the hair, while leaving the hair in excellent condition after shampooing. As measured by a Raymond flowmeter, the rate of flow of the shampoo is among the lowest of the present invention products (in the higher portion of the given viscosity range). The shampoo, and others of this invention, is smarting to the eyes but is non-irritating to the conjunctiva. When in place of the polyoxyethylene (80) sorbitan monolaurate there is employed a corresponding polyoxyethylene (80) sorbitan monopalmitate, having 80 mols of ethylene oxide per mol or polyoxyethylene (44) sorbitan monolaurate, having 44 mols of ethylene oxide per mol, the same general results are obtained.

EXAMPLE 12

|  | Parts |
| --- | --- |
| Polyoxyethylene (20) sorbitan monolaurate | 19.0 |
| Dihydroxyethyl coconut derived alkyl amine oxide (40% active ingredient) | 18.8 |
| Cocomonoethanolamide | 3.5 |
| Polyethylene glycol 6,000 distearate | 2.0 |
| Polyacrylamide | 0.2 |
| Formalin | 0.1 |
| Perfume | 1.0 |
| Deionized water | 55.4 |

The above product, made by the manufacturing methods previously described, is a shampoo of good flow properties and thickness (comparatively high) and is also of good foaming, cleaning and hair treating characteristics.

EXAMPLE 13

|  | Parts |
| --- | --- |
| Polyoxyethylene (20) sorbitan monolaurate | 19.0 |
| Cocoamidopropyl dimethyl amine oxide (30% active ingredient) | 10.0 |
| Dimethyl myristyl amine oxide (30% active ingredient) | 15.0 |
| Polyacrylamide | 0.2 |
| Cocomonoethanolamide | 2.5 |
| Polyethylene glycol 6,000 distearate | 2.0 |
| Formalin | 0.1 |
| Perfime | 1.0 |
| Deionized water | 50.2 |

The above product is an excellent shampoo of good foaming and flow characteristics, which is mild to the hair and non-irritating to the eyes.

While the ultimate goal of this invention, namely, 0% of ionic materials in the final product, is attainable and is practicable, compositions containing small proportions of ionic materials—although being less satisfactory—will not be outside the scope of the broader claims. Thus, a small proportion of ionic material, such as a synthetic anionic detergent, a cationic surface active agent, a salt, a thickener, several of these or mixtures thereof may be present. Preferably no more than 0.5% of any such total will be present but in some cases as much as 1% may be used and more rarely, even 2% of ionic material may be tolerated (as when the ions are large).

The invention has been described with respect to various examples and embodiments but is not to be limited to these because it is evident that one of skill in the art with the present application before him will be able to utilize substituted and equivalents without departing from the spirit of the invention.

What is claimed is:

1. A nonionic shampoo suitable for leaving washed hair in a manageable state consisting essentially of, by weight 3 to 30% of an amine oxide having two short chain and one long chain substituents on the nitrogen thereof wherein the short chain substituents are selected from the group consisting of lower alkyls and lower hydroxyalkyls of 1 to 4 carbon atoms and the long chain substituent is selected from the group consisting of higher alkyls and higher acylamido lower alkyls in which the higher alkyls are of 10 to 20 carbon atoms and the lower alkyls are of 1 to 4 carbon atoms; 2 to 30% of a polyoxyethylene hexitan mono-higher fatty acid ester having from 10 to 20 carbon atoms in the higher fatty acyl thereof and from 10 to 100 moles of ethylene oxide per moles; a nonionic detergent selected from the group consisting of 6 to 30% of higher alkoxy polyoxyethylene ethanols wherein the higher alkoxy is of 10 to 20 carbon atoms and the ethylene oxide content including the $CH_2CH_2O$—of the ethanol, is from 6 to 20 mols per moles, 6 to 30% of $C_{10}$–$C_{20}$ alkyl glycosides, 6 to 30% of mixtures of said polyoxyethylene ethanols and said alkyl glycosides, and a mixture of 1 to 6% of a $C_{10}$–$C_{20}$ acyl $C_2$–$C_3$ mono- or di- alkanolamide and 0.05% to 1% of a polyacrylamide having a weight average molecular weight in the range of 100,000 to 3,000,000; and 25 to 89% water; said shampoo being essentially free of ions and having a conductivity below 2,000 microhmos/cm., having a pH in the range of 5 to 10 and exhibiting good foaming power in the presence of sebum soil at use concentration.

2. A nonionic shampoo according to claim 1 which contains, in addition, 0.01% to 0.05% by weight of formaldehyde and 0.01% to 0.05% by weight of benzophenone.

3. A nonionic shampoo according to claim 1 wherein said pH is in the range of 6.5 to 7.5, said amine oxide is present in an amount of 4% to 15% by weight, said hexitan fatty acid ester is present in an amount of 10% to 30% by weight, and said nonionic detergent is a mixture of said fatty acid alkanolamide and said polyacrylamide.

4. A nonionic shampoo according to claim 3 wherein said pH is in the range of 6.8 to 7.3, said amine oxide is present in an amount of 5% to 10% by weight, said hexitan fatty acid ester is present in an amount of 15% to 25% by weight, said fatty acid alkanolamide is present in an amount of 1.5% to 4% by weight, said polyacrylamide is present in an amount of 0.1% to 0.5% by weight and deionized water is present in an amount of 60% to 75% by weight.

5. A nonionic shampoo according to claim 4 wherein said amine oxide has lower alkyls of 1 to 2 carbon atoms and a higher alkyl of 12 to 18 carbon atoms, said hexitan fatty acid ester is a polyoxyethylene sorbitan fatty acid ester having 12 to 18 carbon atoms in the fatty acyl and containing about 15 to 25 mols of ethylene oxide and said fatty acid alkanolamide is a monoalkanolamide.

6. A nonionic shampoo according to claim 5 which contains, in addition, 0.5% to 5% by weight of a polyethylene glycol higher fatty acid diester of an average molecular weight in the range of 2,000 to 8,000 and wherein the fatty acid moieties are each of 12 to 20 carbon atoms.

7. A nonionic shampoo according to claim 6 wherein said amine oxide is myristyl dimethyl amine oxide, said hexitan fatty acid ester is a polyoxyethylene sorbitan monolaurate, said fatty acid alkanolamide is a monoethanolamide and said diester is a polyethylene glycol distearate and is present in an amount of 1% to 4% by weight.

8. A nonionic shampoo according to claim 1 wherein said pH is in the range of about 6.5 to 7.5, said amine oxide is present in an amount of 5% to 10% by weight, said polyoxyethylene hexitan fatty acid ester is present in an amount of 5% to 10% by weight and said nonionic detergent is present in an amount of 15% to 20% by weight and is selected from the group consisting of said polyoxyethylene ethanols, said alkyl glycosides and mixtures thereof.

9. A nonionic shampoo according to claim 8 wherein said pH is in the range of 6.8 to 7.3, said amine oxide is myristyl dimethyl amine oxide, said hexitan fatty acid ester is a polyoxyethylene sorbitan monolaurate containing 20 moles of ethylene oxide, said nonionic detergent is tridecyl polyoxyethylene ethanol containing 10 moles of ethylene oxide and water is present in an amount of 60% to 75% by weight.

10. A nonionic shampoo according to claim 9 which contains, in addition, about 1.5% to 4% by weight of $C_{10}$–$C_{20}$ acyl monoethanolamide and 0.1% to 0.5% by weight of polyacrylamide having an average molecular weight in the range of 100,000 to 3,000,000.

11. A nonionic shampoo according to claim 8 wherein said pH is in the range of 6.8 to 7.3, said amine oxide is myristyl dimethyl amine oxide, said hexitan fatty acid ester is a polyoxyethylene monolaurate containing 20 moles of ethylene oxide, said nonionic detergent is a higher alkyl glycoside having 10 to 14 carbon atoms in the alkyl group and deionized water is present in an amount of 60% to 75% by weight.

12. A nonionic shampoo according to claim 11 which contains, in addition, about 1.5% to 4% by weight of $C_{10}$–$C_{20}$ acyl monoethanolamide and 0.1% to 0.5% by weight of polyacrylamide having an average molecular weight in the range of 100,000 to 3,000,000.

* * * * *